(12) United States Patent
Streeter et al.

(10) Patent No.: US 7,758,606 B2
(45) Date of Patent: *Jul. 20, 2010

(54) INTRAVASCULAR FILTER WITH DEBRIS ENTRAPMENT MECHANISM

(75) Inventors: Richard B. Streeter, Winchester, MA (US); Gregory H. Lambrecht, Natick, MA (US); John R. Liddicoat, Sewickley, PA (US); Robert Kevin Moore, Natick, MA (US); Todd F. Davenport, Andover, MA (US)

(73) Assignee: Medtronic, Inc., Minneapolis, MN (US)

( * ) Notice: Subject to any disclaimer, the term of this patent is extended or adjusted under 35 U.S.C. 154(b) by 1286 days.

This patent is subject to a terminal disclaimer.

(21) Appl. No.: 10/772,782

(22) Filed: Feb. 5, 2004

(65) Prior Publication Data

US 2005/0010246 A1    Jan. 13, 2005

Related U.S. Application Data

(63) Continuation of application No. 09/896,258, filed on Jun. 29, 2001, now Pat. No. 6,692,513.

(60) Provisional application No. 60/215,542, filed on Jun. 30, 2000, provisional application No. 60/231,101, filed on Sep. 8, 2000.

(51) Int. Cl.
*A61M 29/00*    (2006.01)
*A61F 2/24*    (2006.01)

(52) U.S. Cl. ..................... 606/200; 623/1.11

(58) Field of Classification Search ............... 606/200, 606/108, 191, 195, 198, 110; 623/2.12, 2.14, 623/2.15, 2.16, 2.17, 2.18, 2.19
See application file for complete search history.

(56) References Cited

U.S. PATENT DOCUMENTS 3,334,629 A    8/1967    Cohn

| 3,409,013 A | 11/1968 | Berry |
| 3,540,431 A | 11/1970 | Mobin-Uddin |
| 3,587,115 A | 6/1971 | Shiley |
| 3,628,535 A | 12/1971 | Ostrowsky et al. |

(Continued)

FOREIGN PATENT DOCUMENTS

| DE | 195 32 846 | 3/1997 |
| DE | 195 46 692 | 6/1997 |
| DE | 198 57 887 | 7/2000 |
| DE | 199 07 646 | 8/2000 |
| DE | 10049812 | 4/2002 |

(Continued)

OTHER PUBLICATIONS

Antonatos PG, et al., Effect of the positioning of a balloon valve in the aorta on coronary flow during aortic regurgitation, J Thorac Cardiovasc Surg; Jul. 1984; 88(1): 128-33.

(Continued)

*Primary Examiner*—Vy Q Bui
(74) *Attorney, Agent, or Firm*—Mike Jaro; Jeffrey J. Hohenshell

(57) ABSTRACT

Apparatus for filtering and entrapping debris in the vascular system of a patient, the apparatus including a filter to allow blood to flow therethrough and to restrict passage of debris, wherein the filter captures debris carried in a first direction of blood flow. The apparatus further includes an entrapment mechanism which allows passage of debris and blood therethrough, in the first direction of blood flow and prevents debris passage in a second direction. The entrapment mechanism and filter allow blood and debris therethrough in the first direction of blood flow. The entrapment mechanism prevents debris flow in the second direction of blood flow. A method for filtering and entrapping debris in the vascular system includes inserting the apparatus into the vascular system, allowing blood and debris carried therein to flow through the entrapment mechanism, and removing the apparatus and accumulated debris from the vascular system.

15 Claims, 8 Drawing Sheets

U.S. PATENT DOCUMENTS

| | | |
|---|---|---|
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,996,938 A | 12/1976 | Clark, III |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,291,420 A | 9/1981 | Reul |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,527,549 A | 7/1985 | Gabbay |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Baykut |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,902,272 A | 2/1990 | Milder et al. |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,108,419 A | 4/1992 | Reger et al. |
| 5,152,771 A | 10/1992 | Sabbaghian et al. |
| 5,160,342 A | 11/1992 | Reger et al. |
| 5,161,547 A | 11/1992 | Tower |
| 5,163,953 A | 11/1992 | Vince |
| 5,167,628 A | 12/1992 | Boyles |
| 5,217,483 A | 6/1993 | Tower |
| 5,232,445 A | 8/1993 | Bonzel |
| 5,254,097 A | 10/1993 | Schock et al. |
| 5,272,909 A | 12/1993 | Nguyen et al. |
| 5,295,958 A | 3/1994 | Shturman |
| 5,300,086 A | 4/1994 | Gory et al. |
| 5,324,304 A | 6/1994 | Rasmussen |
| 5,327,774 A | 7/1994 | Nguyen et al. |
| 5,329,942 A | 7/1994 | Gunther et al. |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,480,424 A | 1/1996 | Cox |
| 5,489,294 A | 2/1996 | McVenes et al. |
| 5,496,346 A | 3/1996 | Horzewski et al. |
| 5,500,014 A | 3/1996 | Quijano et al. |
| 5,507,767 A | 4/1996 | Maeda et al. |
| 5,509,428 A | 4/1996 | Dunlop |
| 5,545,209 A | 8/1996 | Roberts et al. |
| 5,545,211 A | 8/1996 | An et al. |
| 5,545,214 A | 8/1996 | Stevens |
| 5,549,626 A | 8/1996 | Miller et al. |
| 5,549,665 A | 8/1996 | Vesely et al. |
| 5,554,185 A | 9/1996 | Block et al. |
| 5,571,215 A | 11/1996 | Sterman et al. |
| 5,575,818 A | 11/1996 | Pinchuk |
| 5,580,922 A | 12/1996 | Park et al. |
| 5,584,879 A | 12/1996 | Reimold et al. |
| 5,591,195 A | 1/1997 | Taheri et al. |
| 5,607,465 A | 3/1997 | Camilli |
| 5,609,626 A | 3/1997 | Quijano et al. |
| 5,645,559 A | 7/1997 | Hachtman et al. |
| 5,667,523 A | 9/1997 | Bynon et al. |
| 5,674,277 A | 10/1997 | Freitag |
| 5,682,906 A | 11/1997 | Sterman et al. |
| 5,695,498 A | 12/1997 | Tower |
| 5,702,368 A | 12/1997 | Stevens et al. |
| 5,713,951 A | 2/1998 | Garrison et al. |
| 5,713,953 A | 2/1998 | Vallana et al. |
| 5,718,725 A | 2/1998 | Sterman et al. |
| 5,728,153 A | 3/1998 | Menkis et al. |
| 5,749,890 A | 5/1998 | Shaknovich |
| 5,766,151 A | 6/1998 | Valley et al. |
| 5,769,816 A * | 6/1998 | Barbut et al. ............ 604/93.01 |
| 5,782,809 A | 7/1998 | Umeno et al. |
| 5,797,960 A | 8/1998 | Stevens et al. |
| 5,800,456 A | 9/1998 | Maeda et al. |
| 5,800,457 A | 9/1998 | Gelbfish |
| 5,800,525 A | 9/1998 | Bachinski et al. |
| 5,814,064 A | 9/1998 | Daniel et al. |
| 5,814,097 A | 9/1998 | Sterman et al. |
| 5,817,126 A | 10/1998 | Imran |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,827,237 A | 10/1998 | Macoviak et al. |
| 5,827,324 A | 10/1998 | Cassell et al. |
| 5,840,081 A | 11/1998 | Andersen et al. |
| 5,846,260 A | 12/1998 | Maahs |
| 5,848,964 A | 12/1998 | Samuels |
| 5,855,597 A | 1/1999 | Jayaraman |
| 5,855,601 A | 1/1999 | Bessler et al. |
| 5,860,996 A | 1/1999 | Tower |
| 5,861,028 A | 1/1999 | Angell |
| 5,868,783 A | 2/1999 | Tower |
| 5,876,367 A | 3/1999 | Kaganov et al. |

| | | | | | | |
|---|---|---|---|---|---|---|
| 5,876,448 | A | 3/1999 | Thompson et al. | 6,398,807 | B1 | 6/2002 | Chouinard et al. |
| 5,888,201 | A | 3/1999 | Stinson et al. | 6,409,750 | B1 | 6/2002 | Hyodoh et al. |
| 5,891,191 | A | 4/1999 | Stinson | 6,425,916 | B1 | 7/2002 | Garrison et al. |
| 5,893,869 | A | 4/1999 | Barnhart et al. | 6,440,164 | B1 | 8/2002 | DiMatteo et al. |
| 5,907,893 | A | 6/1999 | Zadno-Azizi et al. | 6,454,799 | B1 | 9/2002 | Schreck |
| 5,910,154 | A | 6/1999 | Tsugita et al. | 6,458,153 | B1 | 10/2002 | Bailey et al. |
| 5,911,734 | A | 6/1999 | Tsugita et al. | 6,461,382 | B1 | 10/2002 | Cao |
| 5,913,842 | A | 6/1999 | Boyd et al. | 6,468,303 | B1 | 10/2002 | Amplatz et al. |
| 5,925,063 | A | 7/1999 | Khosravi | 6,475,239 | B1 | 11/2002 | Campbell et al. |
| 5,928,261 | A | 7/1999 | Ruiz | 6,482,228 | B1 | 11/2002 | Norred |
| 5,935,139 | A | 8/1999 | Bates | 6,494,909 | B2 | 12/2002 | Greenhalgh |
| 5,941,896 | A | 8/1999 | Kerr | 6,503,272 | B2 | 1/2003 | Duerig et al. |
| 5,944,738 | A | 8/1999 | Amplatz et al. | 6,508,833 | B2 | 1/2003 | Pavcnik et al. |
| 5,947,995 | A | 9/1999 | Samuels | 6,527,800 | B1 | 3/2003 | McGuckin, Jr. et al. |
| 5,954,741 | A | 9/1999 | Fox | 6,530,949 | B2 | 3/2003 | Konya et al. |
| 5,954,745 | A | 9/1999 | Gertler et al. | 6,559,603 | B1 | 5/2003 | Iwami |
| 5,954,766 | A | 9/1999 | Zadno-Azizi et al. | 6,562,058 | B2 | 5/2003 | Seguin et al. |
| 5,957,949 | A | 9/1999 | Leonhardt et al. | 6,569,196 | B1 | 5/2003 | Vesely |
| 5,968,068 | A | 10/1999 | Dehdashtian et al. | 6,582,462 | B1 | 6/2003 | Andersen et al. |
| 5,976,172 | A | 11/1999 | Homsma et al. | 6,585,758 | B1 | 7/2003 | Chouinard et al. |
| 5,980,555 | A | 11/1999 | Barbut et al. | 6,589,264 | B1 | 7/2003 | Barbut et al. |
| 5,984,957 | A | 11/1999 | Laptewicz, Jr. et al. | 6,592,546 | B1 | 7/2003 | Barbut et al. |
| 5,984,959 | A | 11/1999 | Robertson et al. | 6,605,112 | B1 | 8/2003 | Moll et al. |
| 5,989,281 | A | 11/1999 | Barbut et al. | 6,622,604 | B1 | 9/2003 | Chouinard et al. |
| 5,997,573 | A | 12/1999 | Quijano et al. | 6,627,873 | B2 | 9/2003 | Tchakarov et al. |
| 6,022,370 | A | 2/2000 | Tower | 6,632,243 | B1 | 10/2003 | Zadno-Azizi et al. |
| 6,027,525 | A | 2/2000 | Suh et al. | 6,635,068 | B1 | 10/2003 | Dubrul et al. |
| 6,029,671 | A | 2/2000 | Stevens et al. | 6,652,571 | B1 | 11/2003 | White et al. |
| 6,042,589 | A | 3/2000 | Marianne | 6,652,578 | B2 | 11/2003 | Bailey et al. |
| 6,042,598 | A | 3/2000 | Tsugita et al. | 6,656,213 | B2 | 12/2003 | Solem |
| 6,051,014 | A | 4/2000 | Jang | 6,663,663 | B2 | 12/2003 | Kim et al. |
| 6,051,104 | A | 4/2000 | Jang | 6,669,724 | B2 | 12/2003 | Park et al. |
| 6,059,809 | A | 5/2000 | Amor et al. | 6,673,089 | B1 | 1/2004 | Yassour et al. |
| 6,110,201 | A | 8/2000 | Quijano et al. | 6,673,109 | B2 | 1/2004 | Cox |
| 6,123,723 | A | 9/2000 | Konya et al. | 6,676,698 | B2 | 1/2004 | McGuckin, Jr. et al. |
| 6,146,366 | A | 11/2000 | Schachar | 6,682,558 | B2 | 1/2004 | Tu et al. |
| 6,159,239 | A | 12/2000 | Greenhalgh | 6,682,559 | B2 | 1/2004 | Myers et al. |
| 6,162,208 | A | 12/2000 | Hipps | 6,685,739 | B2 | 2/2004 | DiMatteo et al. |
| 6,162,245 | A | 12/2000 | Jayaraman | 6,689,144 | B2 | 2/2004 | Gerberding |
| 6,164,339 | A | 12/2000 | Greenhalgh | 6,689,164 | B1 | 2/2004 | Seguin |
| 6,168,614 | B1 | 1/2001 | Andersen et al. | 6,692,512 | B2 | 2/2004 | Jang |
| 6,171,335 | B1 | 1/2001 | Wheatley et al. | 6,692,513 | B2 | 2/2004 | Streeter et al. |
| 6,192,944 | B1 | 2/2001 | Greenhalgh | 6,695,878 | B2 | 2/2004 | McGuckin, Jr. et al. |
| 6,200,336 | B1 | 3/2001 | Pavcnik et al. | 6,702,851 | B1 | 3/2004 | Chinn et al. |
| 6,218,662 | B1 | 4/2001 | Tchakarov et al. | 6,719,789 | B2 | 4/2004 | Cox |
| 6,221,006 | B1 | 4/2001 | Dubrul et al. | 6,730,118 | B2 | 5/2004 | Spenser et al. |
| 6,221,091 | B1 | 4/2001 | Khosravi | 6,730,377 | B2 | 5/2004 | Wang |
| 6,235,045 | B1 | 5/2001 | Barbut et al. | 6,733,525 | B2 | 5/2004 | Yang et al. |
| 6,241,757 | B1 | 6/2001 | An et al. | 6,736,846 | B2 | 5/2004 | Cox |
| 6,245,102 | B1 | 6/2001 | Jayaraman | 6,752,828 | B2 | 6/2004 | Thornton |
| 6,258,114 | B1 | 7/2001 | Konya et al. | 6,758,855 | B2 | 7/2004 | Fulton, III et al. |
| 6,258,115 | B1 | 7/2001 | Dubrul | 6,769,434 | B2 | 8/2004 | Liddicoat et al. |
| 6,258,120 | B1 | 7/2001 | McKenzie et al. | 6,786,925 | B1 | 9/2004 | Schoon |
| 6,277,555 | B1 | 8/2001 | Duran et al. | 6,790,229 | B1 | 9/2004 | Berreklouw |
| 6,287,321 | B1 | 9/2001 | Jang | 6,792,979 | B2 | 9/2004 | Konya et al. |
| 6,299,637 | B1 | 10/2001 | Shaolia et al. | 6,797,002 | B2 | 9/2004 | Spence |
| 6,302,906 | B1 | 10/2001 | Goicoechea et al. | 6,821,297 | B2 | 11/2004 | Snyders |
| 6,309,382 | B1 | 10/2001 | Garrison et al. | 6,830,575 | B2 | 12/2004 | Stenzel et al. |
| 6,309,399 | B1 | 10/2001 | Barbut et al. | 6,830,584 | B1 | 12/2004 | Seguin |
| 6,309,417 | B1 | 10/2001 | Spence et al. | 6,830,585 | B1 | 12/2004 | Artof |
| 6,327,772 | B1 | 12/2001 | Zadno-Azizi et al. | 6,846,325 | B2 | 1/2005 | Liddicoat |
| 6,334,869 | B1 | 1/2002 | Leonhardt et al. | 6,866,650 | B2 | 3/2005 | Stevens |
| 6,338,735 | B1 | 1/2002 | Stevens | 6,872,223 | B2 | 3/2005 | Roberts |
| 6,348,063 | B1 | 2/2002 | Yassour et al. | 6,875,231 | B2 | 4/2005 | Anduiza et al. |
| 6,352,708 | B1 | 3/2002 | Duran et al. | 6,883,522 | B2 | 4/2005 | Spence et al. |
| 6,361,545 | B1 | 3/2002 | Macoviak et al. | 6,887,266 | B2 | 5/2005 | Williams et al. |
| 6,364,896 | B1 | 4/2002 | Addis | 6,890,330 | B2 | 5/2005 | Streeter et al. |
| 6,371,970 | B1 | 4/2002 | Khosravi et al. | 6,893,460 | B2 | 5/2005 | Spenser et al. |
| 6,371,983 | B1 | 4/2002 | Lane | 6,896,690 | B1 | 5/2005 | Lambrecht et al. |
| 6,375,670 | B1 | 4/2002 | Greenhalgh | 6,908,481 | B2 | 6/2005 | Cribier |
| 6,379,383 | B1 | 4/2002 | Palmaz et al. | 6,913,600 | B2 | 7/2005 | Valley et al. |
| 6,380,457 | B1 | 4/2002 | Yurek et al. | 6,929,653 | B2 | 8/2005 | Streeter |
| 6,395,014 | B1 | 5/2002 | Macoviak et al. | 6,936,066 | B2 | 8/2005 | Palmaz et al. |

| Patent/Publication | Date | Name |
|---|---|---|
| 6,939,365 B1 | 9/2005 | Fogarty et al. |
| 6,951,571 B1 | 10/2005 | Srivastava |
| 6,986,742 B2 | 1/2006 | Hart et al. |
| 6,989,027 B2 | 1/2006 | Allen |
| 6,989,028 B2 | 1/2006 | Lashinski et al. |
| 6,991,649 B2 | 1/2006 | Sleevers |
| 6,994,718 B2 | 2/2006 | Groothuis et al. |
| 7,011,672 B2 | 3/2006 | Barbut et al. |
| 7,011,681 B2 | 3/2006 | Vesely |
| 7,041,128 B2 | 5/2006 | Mcguckin, Jr. et al. |
| 7,044,966 B2 | 5/2006 | Svanjdze et al. |
| 7,048,014 B2 | 5/2006 | Hyodoh et al. |
| 7,097,659 B2 | 8/2006 | Woolfson et al. |
| 7,115,141 B2 | 10/2006 | Menz et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,384,411 B1 | 6/2008 | Condado |
| 2001/0002445 A1 | 3/2001 | Vesely |
| 2001/0007956 A1 | 7/2001 | Letac et al. |
| 2001/0010017 A1 | 7/2001 | Letac et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044591 A1 | 11/2001 | Stevens et al. |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0077696 A1 | 6/2002 | Zadno-Azizi et al. |
| 2002/0095209 A1 | 7/2002 | Zadno-Azizi et al. |
| 2002/0111674 A1 | 8/2002 | Chouinard et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130729 A1 | 7/2003 | Paniagua et al. |
| 2003/0149476 A1 | 7/2003 | Damm et al. |
| 2003/0149475 A1 | 8/2003 | Hyodoh et al. |
| 2003/0149478 A1 | 8/2003 | Figulla et al. |
| 2003/0153974 A1 | 8/2003 | Spenser et al. |
| 2003/0176884 A1 | 9/2003 | Berrada et al. |
| 2003/0181850 A1 | 9/2003 | Diamond et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0212410 A1 | 11/2003 | Stenzel et al. |
| 2003/0212452 A1 | 11/2003 | Zadno-Azizi et al. |
| 2003/0212454 A1 | 11/2003 | Scott et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Seguin et al. |
| 2004/0093075 A1 | 5/2004 | Kuehne |
| 2004/0097788 A1 | 5/2004 | Mourles et al. |
| 2004/0098112 A1 | 5/2004 | DiMatteo et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Laskinski et al. |
| 2004/0167573 A1 | 8/2004 | Williamson |
| 2004/0167620 A1 | 8/2004 | Ortiz |
| 2004/0186563 A1 | 9/2004 | Lobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0225355 A1 | 11/2004 | Stevens |
| 2004/0254636 A1 | 12/2004 | Flagle et al. |
| 2004/0260317 A1 | 12/2004 | Bloom et al. |
| 2004/0260394 A1 | 12/2004 | Douk et al. |
| 2004/0267357 A1 | 12/2004 | Allen et al. |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |

| | | | | | | |
|---|---|---|---|---|---|---|
| 2005/0107871 A1 | 5/2005 | Realyvasquez et al. | | 2007/0244555 A1 | 10/2007 | Rafiee et al. |
| 2005/0113910 A1 | 5/2005 | Paniagua | | 2007/0244556 A1 | 10/2007 | Rafiee et al. |
| 2005/0119688 A1 | 6/2005 | Bergheim | | 2007/0244557 A1 | 10/2007 | Rafiee et al. |
| 2005/0131438 A1 | 6/2005 | Cohn | | 2007/0250160 A1 | 10/2007 | Rafiee |
| 2005/0137686 A1 | 6/2005 | Salahieh | | 2007/0255394 A1 | 11/2007 | Ryan |
| 2005/0137692 A1 | 6/2005 | Haug | | 2007/0255396 A1 | 11/2007 | Douk et al. |
| 2005/0137695 A1 | 6/2005 | Salahieh | | 2007/0288000 A1 | 12/2007 | Bonan |
| 2005/0137701 A1 | 6/2005 | Salahieh | | 2008/0009940 A1 | 1/2008 | Cribier |
| 2005/0143809 A1 | 6/2005 | Salahieh | | 2008/0015671 A1 | 1/2008 | Bonhoeffer |
| 2005/0148997 A1 | 7/2005 | Valley et al. | | 2008/0021552 A1 | 1/2008 | Gabbay |
| 2005/0165477 A1 | 7/2005 | Anduiza et al. | | 2008/0133003 A1 | 6/2008 | Seguin et al. |
| 2005/0187616 A1 | 8/2005 | Realyvasquez | | 2008/0147105 A1 | 6/2008 | Wilson et al. |
| 2005/0203549 A1 | 9/2005 | Realyvasquez | | 2008/0154356 A1 | 6/2008 | Obermiller et al. |
| 2005/0203605 A1 | 9/2005 | Dolan | | 2008/0161910 A1 | 7/2008 | Revuelta et al. |
| 2005/0203618 A1 | 9/2005 | Sharkawy | | 2008/0161911 A1 | 7/2008 | Revuelta et al. |
| 2005/0222674 A1 | 10/2005 | Paine | | 2008/0183273 A1 | 7/2008 | Mesana et al. |
| 2005/0228495 A1 | 10/2005 | Macoviak | | 2008/0215144 A1 | 9/2008 | Ryan et al. |
| 2005/0234546 A1 | 10/2005 | Nugent | | | | |
| 2005/0240200 A1 | 10/2005 | Bergheim | | FOREIGN PATENT DOCUMENTS | | |
| 2005/0240263 A1 | 10/2005 | Fogarty et al. | | | | |
| 2005/0261759 A1 | 11/2005 | Lambrecht et al. | | DE | 10049813 | 4/2002 |
| 2005/0283962 A1 | 12/2005 | Boudjemline | | DE | 10049815 | 4/2002 |
| 2006/0004439 A1 | 1/2006 | Spenser et al. | | EP | 0408245 | 1/1991 |
| 2006/0009841 A1 | 1/2006 | McGuckin et al. | | EP | 850 607 | 7/1998 |
| 2006/0052867 A1 | 3/2006 | Revuelta et al. | | EP | 1057459 A1 | 6/2000 |
| 2006/0058775 A1 | 3/2006 | Stevens et al. | | EP | 1057460 A1 | 6/2000 |
| 2006/0089711 A1 | 4/2006 | Dolan | | EP | 1088529 | 4/2001 |
| 2006/0100685 A1 | 5/2006 | Seguin et al. | | EP | 1340473 | 9/2003 |
| 2006/0116757 A1 | 6/2006 | Lashinski et al. | | FR | 2788217 | 12/1999 |
| 2006/0135964 A1 | 6/2006 | Vesely | | SU | 1271508 | 11/1986 |
| 2006/0142848 A1 | 6/2006 | Gabbay | | WO | 95/29640 | 11/1995 |
| 2006/0167474 A1 | 7/2006 | Bloom et al. | | WO | 97/17100 | 5/1997 |
| 2006/0195134 A1 | 8/2006 | Crittenden | | WO | WO 99/15223 | 4/1999 |
| 2006/0206192 A1 | 9/2006 | Tower et al. | | WO | WO 99/33414 | 7/1999 |
| 2006/0206202 A1 | 9/2006 | Bonhoefer et al. | | WO | 00/41652 | 7/2000 |
| 2006/0247763 A1 | 11/2006 | Slater | | WO | 00/47136 | 8/2000 |
| 2006/0259134 A1 | 11/2006 | Schwammenthal et al. | | WO | WO 00/44313 | 8/2000 |
| 2006/0259137 A1 | 11/2006 | Artof et al. | | WO | WO 00/47139 | 8/2000 |
| 2006/0271081 A1 | 11/2006 | Realyvasquez | | WO | 02/41789 | 5/2002 |
| 2006/0282161 A1 | 12/2006 | Huynh et al. | | WO | 03/020171 A2 | 3/2003 |
| 2007/0005129 A1 | 1/2007 | Damm et al. | | WO | 2004/019825 | 3/2004 |
| 2007/0005131 A1 | 1/2007 | Taylor | | WO | 2005/004753 | 1/2005 |
| 2007/0010878 A1 | 1/2007 | Raffiee et al. | | WO | 2008/100599 | 8/2008 |
| 2007/0016286 A1 | 1/2007 | Case et al. | | | | |
| 2007/0027518 A1 | 2/2007 | Herrmann et al. | | OTHER PUBLICATIONS | | |
| 2007/0027533 A1 | 2/2007 | Douk | | | | |
| 2007/0043435 A1 | 2/2007 | Seguin et al. | | | | |
| 2007/0051377 A1 | 3/2007 | Douk et al. | | | | |
| 2007/0073392 A1 | 3/2007 | Heyninck-Jantz | | | | |
| 2007/0078509 A1 | 4/2007 | Lotfy et al. | | | | |
| 2007/0078510 A1 | 4/2007 | Ryan | | | | |
| 2007/0088431 A1 | 4/2007 | Bourang et al. | | | | |
| 2007/0093869 A1 | 4/2007 | Bloom et al. | | | | |
| 2007/0100439 A1 | 5/2007 | Cangialosi | | | | |
| 2007/0112415 A1 | 5/2007 | Barlett | | | | |
| 2007/0162102 A1 | 7/2007 | Ryan et al. | | | | |
| 2007/0162113 A1 | 7/2007 | Sharkawy et al. | | | | |
| 2007/0203391 A1 | 8/2007 | Bloom et al. | | | | |
| 2007/0225681 A1 | 9/2007 | House | | | | |
| 2007/0232898 A1 | 10/2007 | Huynh et al. | | | | |
| 2007/0233228 A1 | 10/2007 | Eberhardt et al. | | | | |
| 2007/0233237 A1 | 10/2007 | Krivoruchko | | | | |
| 2007/0233238 A1 | 10/2007 | Huynh et al. | | | | |
| 2007/0238979 A1 | 10/2007 | Huynh et al. | | | | |
| 2007/0239265 A1 | 10/2007 | Birdsall | | | | |
| 2007/0239266 A1 | 10/2007 | Birdsall | | | | |
| 2007/0239269 A1 | 10/2007 | Dolan et al. | | | | |
| 2007/0239273 A1 | 10/2007 | Allen | | | | |
| 2007/0244544 A1 | 10/2007 | Birdsall et al. | | | | |
| 2007/0244545 A1 | 10/2007 | Birdsall et al. | | | | |
| 2007/0244546 A1 | 10/2007 | Francis | | | | |
| 2007/0244553 A1 | 10/2007 | Rafiee et al. | | | | |
| 2007/0244554 A1 | 10/2007 | Rafiee et al. | | | | |

Antonatos PG, et al., Intraventricular Pumping At The Mitral Ring In Mitral Regurgitation; Life Support Syst; 1985; 3 Suppl 1:167-71.

Antonatos PG, et al., The Use Of A Small Intra-Aortic Balloon To Increase Coronary Flow; Life Support Syst; Jul.-Sep. 1983 1(3): 151-64.

Frederiksen J, et al. Use Of A Counterpulsation Balloon As A Substitute For The Pulmonic Valve: A New Application; Ann Thorac Surg; Jun. 1986; 41(6): 616-21.

Matsubara T, et al., Balloon Catheter With Check Valves For Experimental Relief Of Acute Aortic Regurgitation; Am Heart J; Oct. 1992; 124(4): 1002-8.

Moulopoulos SD, et al., Intra-Aortic Balloon Pump for Relief of Aortic Regurgitation. Experimental Study, J Thorac Cardiovasc Surg; Jul. 1980:80(1):38-44.

Siwek LG, et al., Acute Control of Pulmonary Regurgitation With A Balloon "Valve". An experimental investigation, J Thorac Cardiovasc Surg; Sep. 1985;90(3):404-9.

Cartwright RS, et al., Combined Replacement of Aortic And Mitral Valves; J.A.M.A., Apr. 7, 1962;86-90.

Andersen, H.R. et al, "Transluminal implantation of artificial heart valves. Description of a new expandable aortic valve and initial results with implantation by catheter technique in closed chest pigs." Euro. Heart J. (1992) 13:704-708.

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. 1664-1669.

Bonhoeffer, et al, "Percutaneous Mitral Valve Dilatation with the Multi-Track System," Catheterization and Cardiovascular Interventions—Official Journal of the Society for Cardiac Angiography & Interventions (United States), Oct. 1999, pp. 178-183.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Technique and Results of Percutaneous Mitral Valvuloplasty With the Multi-Track System," Journal of Interventional Cardiology (United States), 200, pp. 263-268.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Closure of a Paravalvular Mitral Regurgitation with Amplatzer and Coil Prostheses," Archives des Maladies du Coeur Et Des Vaisseaux (France), May 2002, pp. 483-486.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Cribier, A. et al, "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

Hanzel, et al., "Complications of percutaneous aortic valve replacement: experience with the Criber-Edwards™ percutaneous heart valve," Eurointervention Supplements (2006), 1 (Supplement A) A3-A8.

Huber, et al., "Do Valved Stents Compromise Coronary Flow?" Eur. J. Cardiothorac. Surg. 2004;25:754-759.

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, p. IV-375.

Khambadkone, et al, "Percutaneous Pulmonary Valve Implantation: Impact of Morphology on Case Selection," Circulation 108 (17 Supplement), Oct. 28, 2003, p. IV-642-IV-643.

Lutter, et al, "Percutaneous Aortic Valve Replacement: An Experimental Study. I. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Webb, et al., "Percutaneous Aortic Valve Implantation Retrograde from the Femoral Artery," Circulation (2006), 113;842-850.

Yonga, et al, "Effect of Percutaneous Balloon Mitral Valvotomy on Pulmonary Venous Flow in Severe Mitral Stenosis," East African Medical Journal (Kenya), Jan. 1999, pp. 28-30.

Yonga, et al, "Percutaneous Balloon Mitral Valvotomy: Initial Experience in Nairobi Using a New Multi-Track Catheter System," East African Medical Journal (Kenya), Feb. 1999, pp. 71-74.

Yonga, et al, "Percutaneous Transluminal Balloon Valvuloplasty for Pulmonary Valve Stenosis: Report on Six Cases," East African Medical Journal (Kenya), Apr. 1994, pp. 232-235.

Yonga, et al, "Percutaneous Transvenous Mitral Commissurotomy in Juvenile Mitral Stenosis," East African Medical Journal (Kenya), Apr. 2003, pp. 172-174.

* cited by examiner

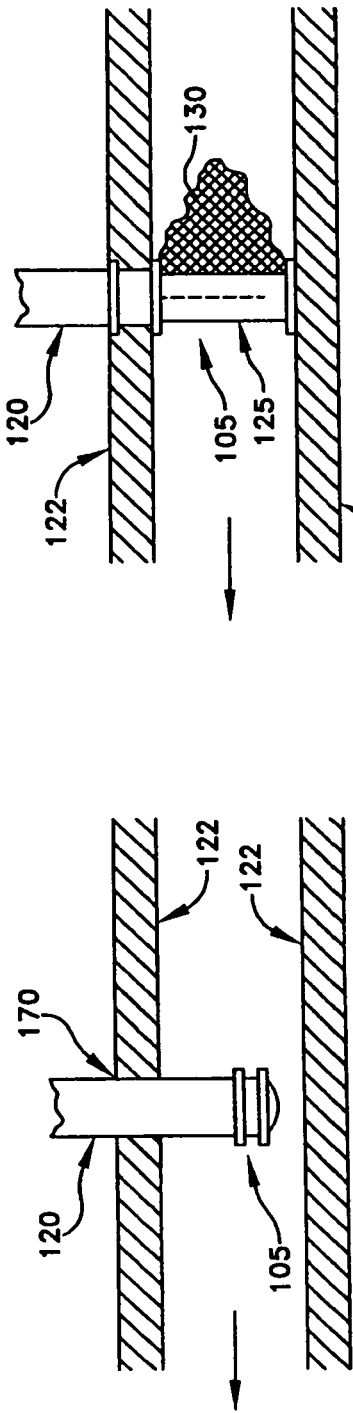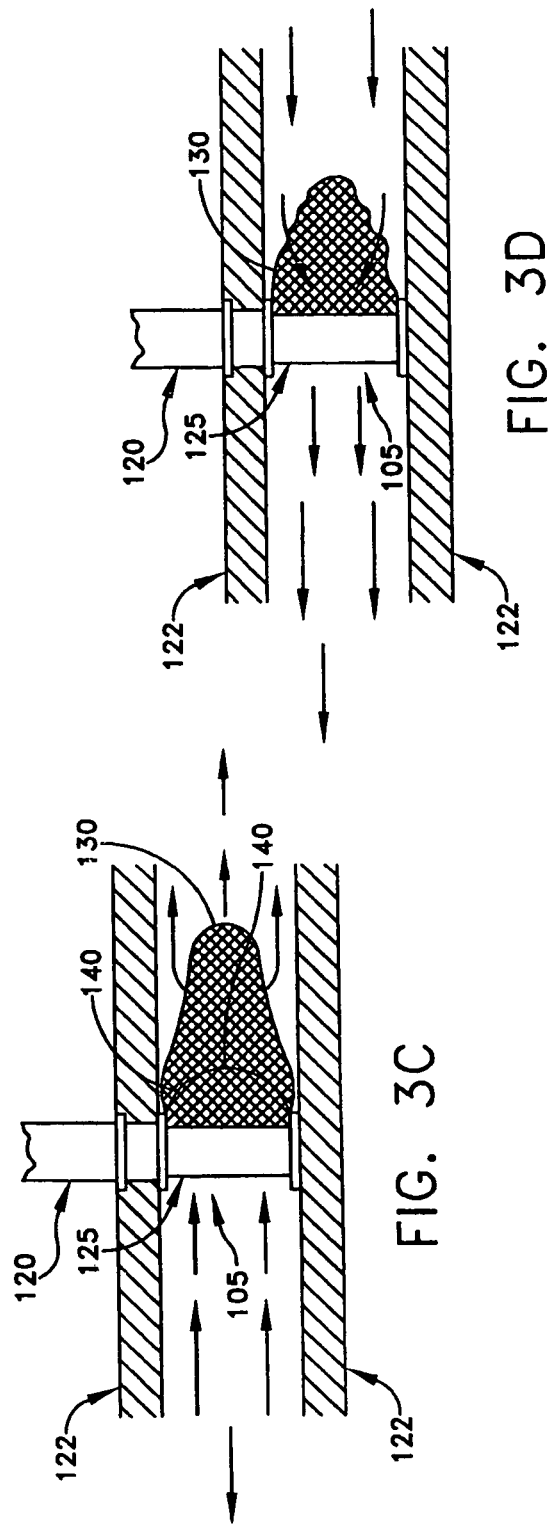

INTRAVASCULAR FILTER WITH DEBRIS ENTRAPMENT MECHANISM

REFERENCE TO PENDING PRIOR PATENT APPLICATION

This is a continuation of prior U.S. patent application Ser. No. 09/896,258, now U.S. Pat. No. 6,692,513 filed Jun. 29, 2001 by Richard B. Streeter et al. for INTRAVASCULAR FILTER WITH DEBRIS ENTRAPMENT MECHANISM, which in turn claims benefit of U.S. Provisional Patent Application Ser. No. 60/215,542, filed Jun. 30, 2000 by Richard B. Streeter et al. for INTRAVASCULAR FILTER WITH DEBRIS ENTRAPMENT MECHANISM, which patent application is hereby incorporated herein by reference, and of U.S. Provisional Patent Application Ser. No. 60/231,101, filed Sep. 8, 2000 by Richard B. Streeter et al. for INTRAVASCULAR FILTER WITH DEBRIS ENTRAPMENT MECHANISM.

FIELD OF THE INVENTION

This invention relates to intravascular filtering apparatus and methods in general, and more particularly to apparatus and methods for filtering and irreversibly entrapping embolic debris from the vascular system during an intravascular or intracardiac procedure.

BACKGROUND OF THE INVENTION

Intracardiac and intravascular procedures, whether performed percutaneously or in an open, surgical, fashion, may liberate particulate debris. Such debris, once free in the vascular system, may cause complications including vascular occlusion, end-organ ischemia, stroke, and heart attack. Ideally, this debris is filtered from the vascular system before it can travel to distal organ beds.

Using known filter mechanisms deployed in the arterial system, debris is captured during systole. There is a danger, however, that such debris may escape the filter mechanism during diastole or during filter removal. Apparatus and methods to reduce debris escape during diastole or during filter removal may be desirable to reduce embolic complications.

SUMMARY OF THE INVENTION

An object of the invention is to provide a filtering mechanism that irreversibly entraps debris therein.

Another object of the invention is to provide a filtering mechanism that permanently captures debris from the intravascular system of a patient.

A further object of the invention is to provide a filtering mechanism with greater ability to collect debris in the intravascular system of a patient to decrease the number of complications attributable to such debris.

Another further object of this invention is to provide a filter holding mechanism suitable to be secured to a retractor used to create access to the heart and surrounding structures during heart surgery procedures.

A still further object is to provide a method for using a filtering mechanism in the intravascular system of a patient to permanently capture debris therefrom.

Another still further object of the present invention is to provide a method for introducing a filtering device in the aorta downstream of the aortic valve to restrict the passage of emboli while allowing blood to flow through the aorta during cardiovascular procedures, and to entrap debris collected in the filter so as to prevent its escape during cardiac diastole or during manipulation, repositioning or removal of the device from the aorta.

With the above and other objects in view, as will hereinafter appear, there is provided apparatus for debris removal from the vascular system of a patient, said apparatus comprising: a filtering device having a proximal side and a distal side said filter being sized to allow blood flow therethrough and to restrict debris therethrough and said filter having a first given perimeter, wherein blood flow in a first direction passes from the proximal side to the distal side of the filtering device; an entrapment mechanism having a proximal side and a distal side, the entrapment mechanism forming a selective opening to allow debris and blood flow passage in the first direction from the proximal side to the distal side therethrough, the selective opening having a restriction mechanism to prevent debris passage in a second direction opposite to said first direction the selective opening having a second given perimeter, the first given perimeter and the second given perimeter being deployed within the vascular system so as to form a chamber between the distal side of the entrapment mechanism and the proximal side of the filtering device, wherein the entrapment mechanism allows blood flow and debris to pass therethrough in the first direction, the filtering device allows blood flow to pass therethrough in the first direction, the restriction mechanism prevents debris from passing back through said selective opening in a second direction opposite to the first direction and the chamber contains the debris received through the entrapment mechanism so as to prevent the escape of the debris therein by said filtering device in the first direction and said restriction mechanism in said second direction.

In accordance with another further feature of the invention there is provided a method for filtering and entrapping debris from the vascular system of a patient, the method comprising: providing apparatus for filtering and entrapping debris from the vascular system of a patient, the apparatus comprising: a filter device being sized to allow blood flow therethrough and to restrict passage of debris therethrough, and the filter device having a first given perimeter, a proximal side and a distal side; and wherein the filtering device captures debris carried in a first direction of blood flow from the proximal side to the distal side thereof on the proximal side of the filter device; an entrapment mechanism having a proximal side and a distal side, the entrapment mechanism including a selective opening to allow passage of blood and debris therethrough, the selective opening being configured to allow passage of blood and debris carried therein therethrough in the first direction of blood flow from the proximal side to the distal side of the entrapment mechanism, the selective opening having a restriction mechanism to prevent debris passage from the distal side to the proximal side of the entrapment mechanism in a second direction opposite to the first direction, the selective opening forming a second given perimeter, and the first given perimeter and the second given perimeter being deployed within the vascular system so as to form a chamber between the distal side of the entrapment mechanism and the proximal side of the filtering device; wherein the entrapment mechanism allows blood and debris carried therein therethrough in the first direction of blood flow, the filtering device allows blood therethrough in the first direction of blood flow, and the restriction mechanism prevents debris back through the selective opening in the second direction of blood flow opposite to the first direction of blood flow such that the chamber entraps the filtered debris received therein for debris removal from the vascular system of the patient; inserting said apparatus into the vascular system of the patient; allowing blood and debris carried therein to flow through the entrapment mechanism, and into the chamber; and removing the apparatus from the vascular system of the patient.

The above and other features of the invention, including various novel details of construction and combinations of parts and method steps will now be more particularly described with reference to the accompanying drawings and pointed out in the claims. It will be understood that the particular devices and method steps embodying the invention are shown by way of illustration only and not as limitations of the invention. The principles and features of this invention may be employed in various and numerous embodiments without departing from the scope of the invention.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIGS. 3A-3D are a series of schematic illustrations depicting a method of using the deployable entrapment filtering device of FIGS. 2A and 2B;

DETAILED DESCRIPTION OF THE PREFERRED EMBODIMENTS

A filtration and entrapment apparatus 5 is shown in FIGS. 1A-5D for debris removal from the vascular system of a patient. Filtration and entrapment apparatus 5 generally includes a filter device 10 and an entrapment mechanism 15. Filtration and entrapment apparatus 5 can be used to filter emboli during a variety of intravascular or intracardiac procedures, including, but not limited to, the following procedures: vascular diagnostic procedures, angioplasty, stenting, angioplasty and stenting, endovascular stent-graft and surgical procedures for aneurysm repairs, coronary artery bypass procedures, cardiac valve replacement and repair procedures, and carotid endardarectomy procedures.

Now looking at FIGS. 1A-1D, a preferred embodiment of the present invention is shown with filtration and entrapment apparatus 5 as described herein below.

Figure 1A:
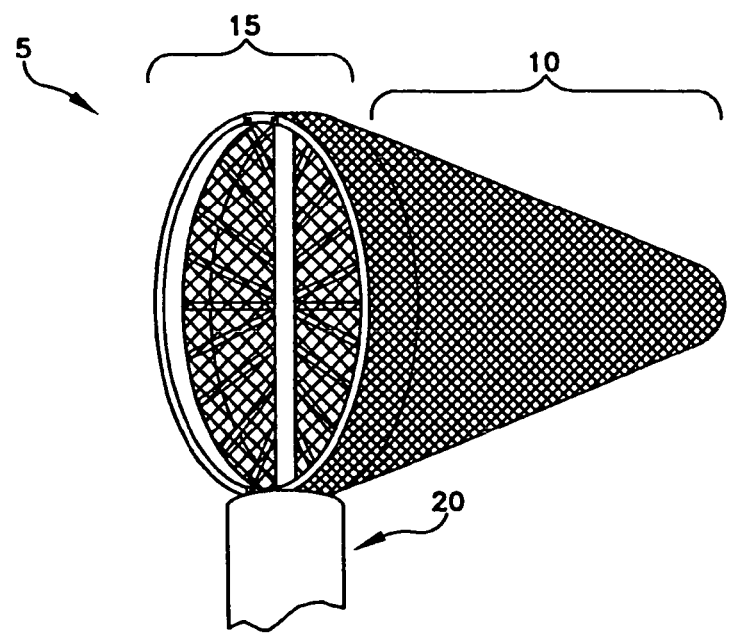
FIG. 1A is a perspective view of a deployable entrapment filtering device for debris removal showing the filtering device in its fully deployed shape as released from its cannula into the blood stream of a patient.

FIG. 1A depicts the profile of filtration and entrapment apparatus 5 in its fully deployed shape, with filter device 10 and entrapment mechanism 15 released from cannula 20 into the blood stream (not shown). Prior to deployment, filter device 10 and entrapment mechanism 15 are collapsed within cannula 20, e.g., by moving the proximal end 25A proximally along center post 50.

Figure 1B:
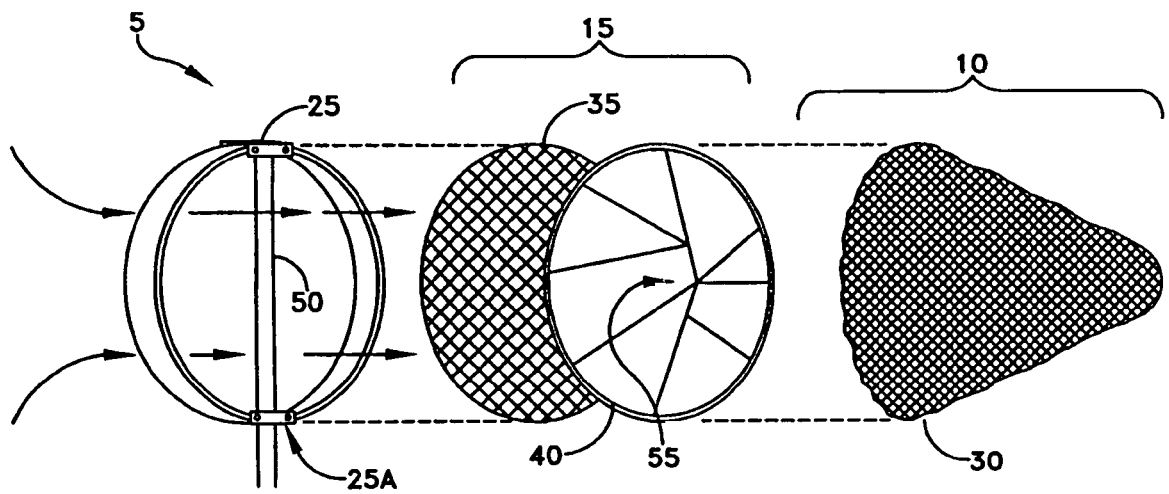
FIG. 1B is an exploded perspective view of the deployable entrapment filtering device of FIG. 1A showing the components thereof.

FIG. 1B depicts the primary components of filtration and entrapment apparatus 5 comprising filter device 10 and entrapment mechanism 15 in attachment to deployable frame 25. In the present embodiment of the invention, filter device 10 comprises a filter mesh bag 30, and entrapment mechanism 15 comprises a piece of coarse mesh 35 and a set of entrapment flaps 40.

Figure 1C:
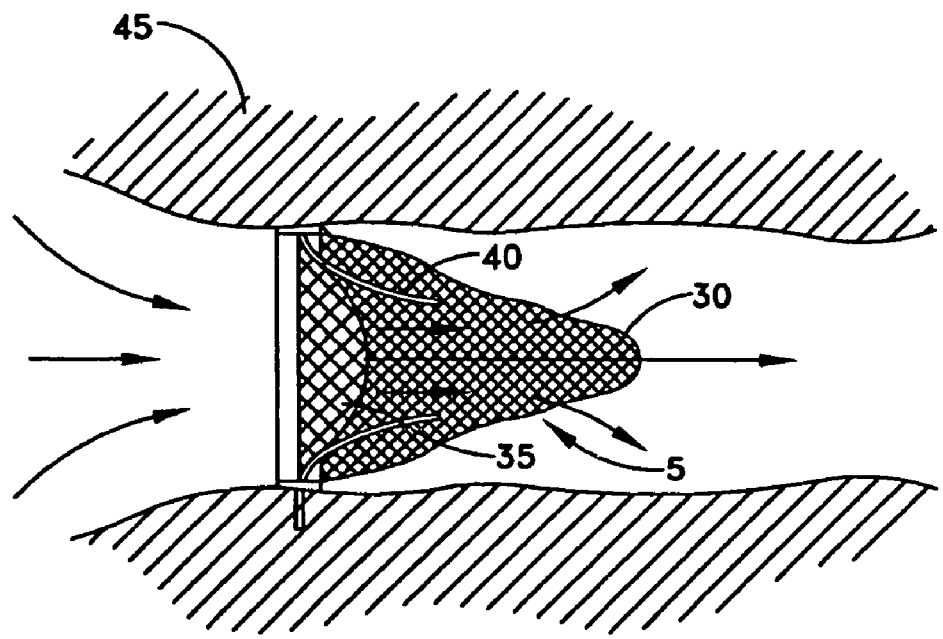
FIG. 1C is a schematic cross-sectional illustration depicting the deployable entrapment filtering device of FIGS. 1A and 1B during cardiac systole.

FIG. 1C depicts filtration and entrapment apparatus 5 deployed within an aorta 45 during cardiac systole. Blood and debris flow through opened deployable frame 25, across course mesh 35, between and through entrapment flaps 40 and into the end of the filter mesh bag 30. Entrapment flaps 40 ensure unidirectional flow of blood and debris into filter mesh bag 30.

Figure 1D:
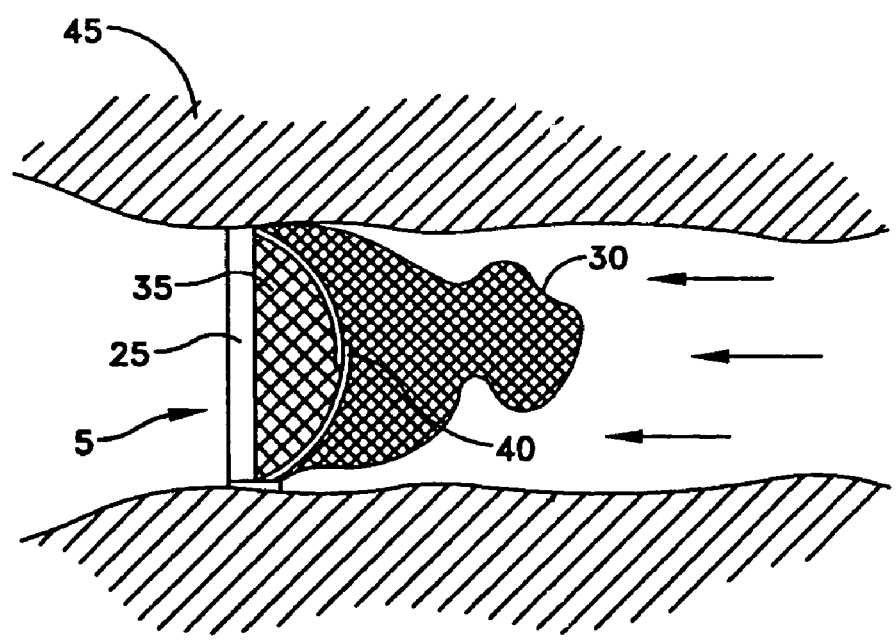
FIG. 1D is a schematic cross-sectional illustration depicting the deployable entrapment filtering device of FIGS. 1A and 1B during cardiac diastole.

FIG. 1D depicts filtration and entrapment apparatus 5 within the aorta 45 responding to any retrograde flow of blood and/or back pressure within the aorta 45 during cardiac diastole. The back flow of blood and/or back pressure causes filter mesh bag 30 to partially deform and entrapment flaps 40 to close against coarse mesh 35. Coarse mesh 35 is of a structure adequate to permit the free flow of blood and debris through it and into filter mesh bag 30, and serves as a supporting structure against which entrapment flaps 40 can close and remain in a closed position to prevent the escape of embolic debris.

Still looking at FIGS. 1A-1D, it should also be appreciated that the entrapment flaps 40 may be attached to structures other than deployable frame 25, e.g., the entrapment flaps 40 may be attached to a center post 50, or to coarse mesh 35, etc. Furthermore, if desired, entrapment flaps 40 may be biased closed or biased open. In addition, entrapment mechanism 15 may consist of one or more flaps 55, and have a configuration including, but not limited to, a single disk diaphragm (not shown), a semi-lunar configuration (not shown), a gill slit configuration (not shown), a multi-leaflet flap configuration (not shown), etc.

It should also be appreciated that, while in the foregoing description the apparatus shown in FIGS. 1A-1D has been described in the context of functioning as a filter, it may also function as a one-way check valve. To the extent that the apparatus shown in FIGS. 1A-1D is intended to function primarily as a one-way check valve, filter mesh bag 30 (see FIG. 1B) may be retained or it may be omitted.

Figure 2A:
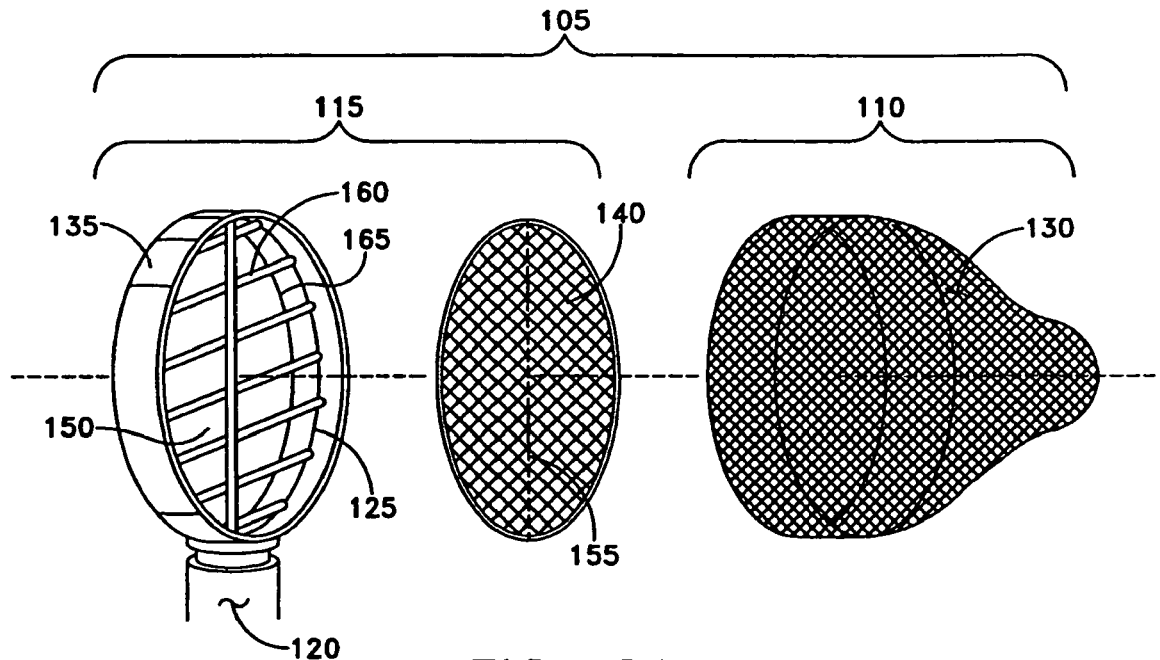
FIG. 2A is an exploded perspective view of a deployable entrapment filtering device for debris removal showing the components thereof including a set of filter mesh entrapment leaflets.
Figure 2B:
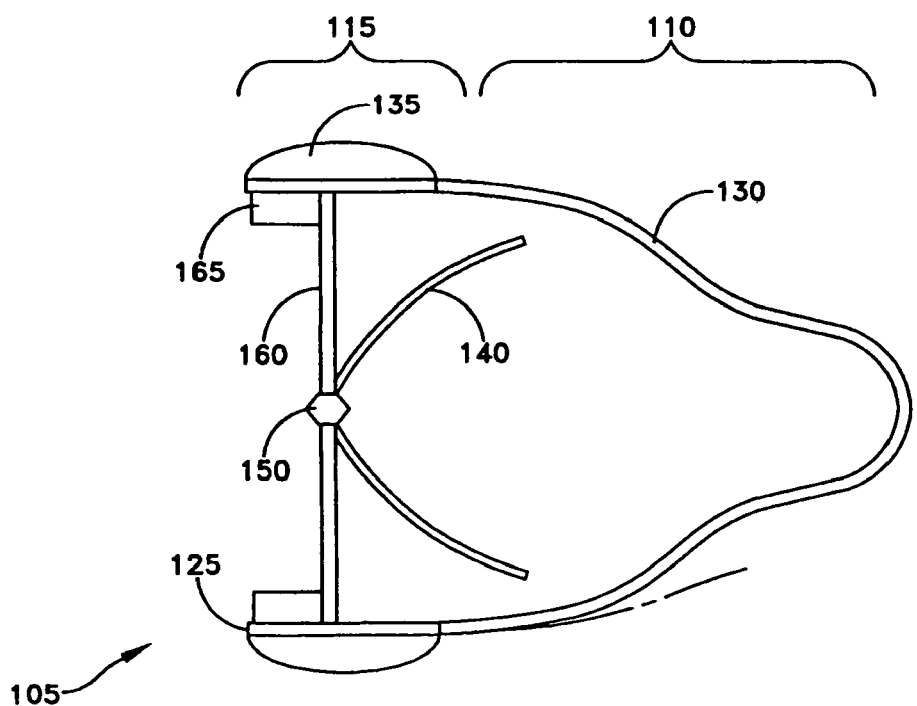
FIG. 2B is a schematic cross-sectional illustration depicting the deployable entrapment filtering device of FIG. 2A during cardiac systole.

Looking next at FIGS. 2A and 2B, there is shown an alternative form of the present invention as a bidirectional flow filtration and entrapment apparatus 105. Bidirectional flow filtration and entrapment apparatus 105 of FIGS. 2A and 2B generally comprises a filter device 110 and an entrapment mechanism 115 delivered by a cannula 120 to the interior of a vascular structure 122 (see FIGS. 3A-3D); a deployable filter frame 125; a filter bag 130 attached to the perimeter of deployable filter frame 125; a compliant, soft outer cuff 135 (preferably formed out of a biologically inert material such as Teflon, Dacron, Silastic, etc.) for sealing filtration and entrapment apparatus 105 against the inner wall of vascular structure 122 when deployable filter frame 125 is expanded; entrapment leaflets 140, preferably in the form of a fine filter mesh; a center post 150 (preferably formed out of steel or the equivalent) passing across the interior of the deployable filter frame 125; a hinge line 155 on entrapment leaflets 140, connected to center post 150, for permitting the entrapment leaflets 140 to open and close; co-aptation strands 160 extending across the interior of deployable filter frame 125 and providing a seat against which entrapment leaflets 140 may close during diastole; and a perimeter seal 165 (preferably formed out of expanded Teflon or the like). Perimeter seal 165 acts like a step to help support entrapment leaflets 140 during diastole.

In addition, it should also be appreciated that soft outer cuff 135 may comprise a radially expandable mechanism (e.g., a balloon, a decompressed sponge, a spring loaded leaflet, etc.) for sealing filtration and entrapment apparatus 105 against the inner wall of vascular structure 122.

As noted above, entrapment leaflets 140 are preferably formed out of a fine filter mesh. This filter mesh is sized so that it will pass blood therethrough but not debris. Furthermore, this filter mesh is sized so that it will provide a modest resistance to blood flow, such that the entrapment leaflets will open during systole and close during diastole. By way of example but not limitation, the filter mesh may have a pore size of between about 40 microns and about 300 microns.

FIGS. 3A-3D illustrate operation of bidirectional flow filtration and entrapment apparatus 105 shown in FIGS. 2A and 2B. More particularly, cannula 120 of deployable filtration and entrapment apparatus 105 is first inserted through a small incision 170 in the wall of the vascular structure 122 (see FIG. 3A). Then deployable filter frame 125 is deployed (see FIG. 3B). Thereafter, during systole (see FIG. 3C), blood flows through deployable filter from 125, forcing entrapment leaflets 140 open, and proceeds through filter bag 130. Any debris contained in the blood is captured by filter bag 130 and thereby prevented from moving downstream past bidirectional flow filtration and entrapment apparatus 105. During diastole (see FIG. 3D), when the blood flow momentarily reverses direction, entrapment leaflets 140 (shown in FIGS. 2A and 2B) close, seating against co-aptation strands 160 (shown in FIGS. 2A and 2B) extending across the interior of deployable filter frame 140 (shown in FIGS. 2A and 2B). The blood passes through the fine mesh of entrapment leaflets 140 (shown in FIGS. 2A and 2B), being filtered as it passes, thus permitting coronary profusion to take place during the diastolic phase. The fine mesh of entrapment leaflets 140 (shown in FIGS. 2A and 2B) prevents debris from passing back through bidirectional flow filtration and entrapment apparatus 105.

It should also be appreciated that with bidirectional flow filtration and entrapment apparatus 105 of FIGS. 2A, 2B and 3A-3D, entrapment leaflets 140 may be attached to structures other than center post 150, e.g., they may be attached to co-aptation strands 160, or to deployable filter frame 125, etc. Furthermore, if desired, entrapment leaflets 140 may be biased closed, or biased open. In addition, entrapment mechanism 15 may consist of one or more flaps (not shown), and have a configuration including, but not limited to, a single disk diaphragm (not shown), a semi-lunar configuration (not shown), a gill slit configuration (not shown), a multi-leaflet flap configuration (not shown), etc.

Figure 4A:
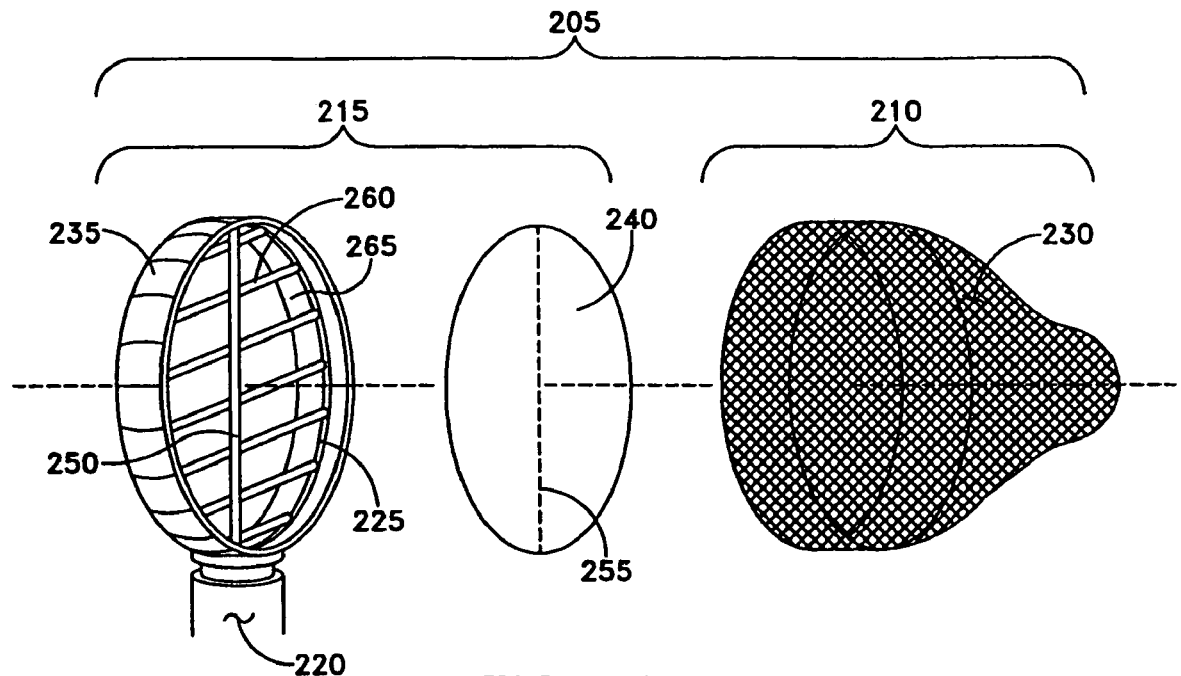
FIG. 4A is an exploded perspective view of a deployable entrapment filtering device for debris removal showing the components thereof including a set of non-porous valve leaflets.
Figure 4B:
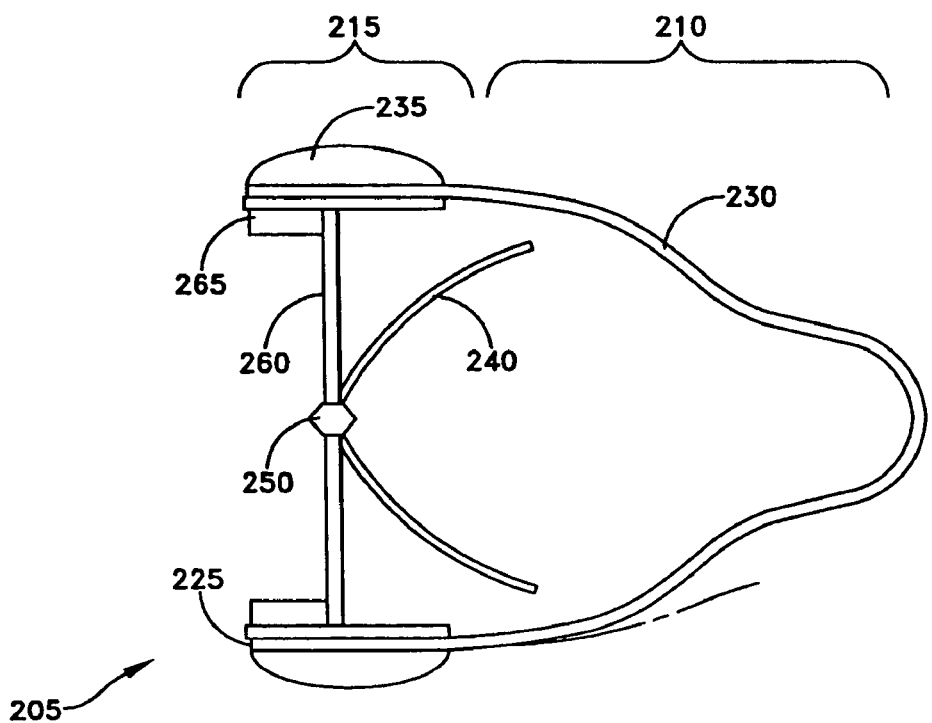
FIG. 4B is a schematic cross-sectional illustration depicting the deployable entrapment filtering device of FIG. 4A during cardiac systole.
Figure 5A:
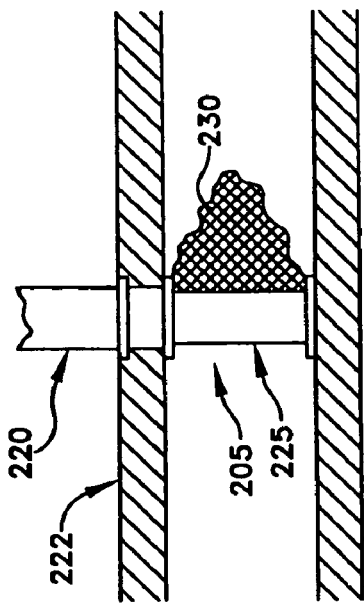
FIGS. 5A-5D are a series of schematic illustrations depicting a method of using the deployable entrapment filtering device of FIGS. 4A and 4B.
Figure 5B:
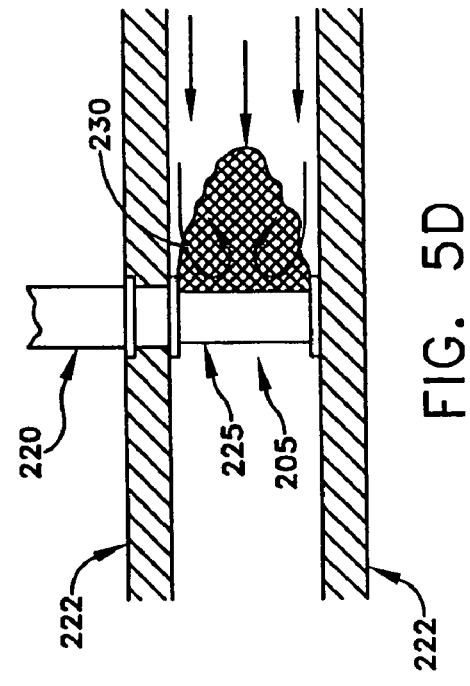
Figure 5C:
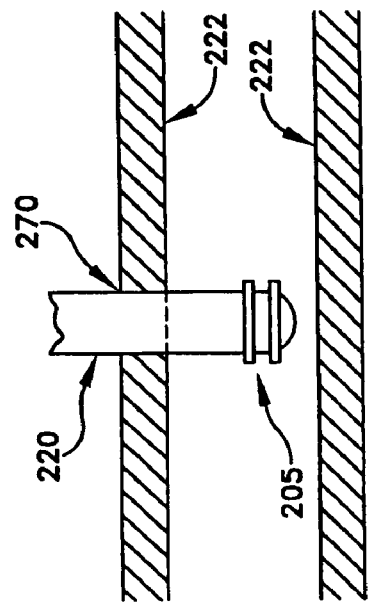
Figure 5D:
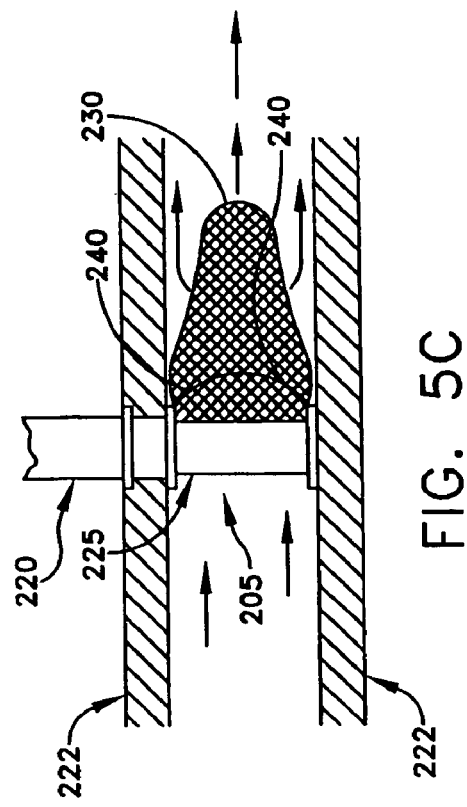

Looking next at FIGS. 4A and 4B, there is shown a deployable valve/filter apparatus 205. Deployable valve/filter apparatus 205 of FIGS. 4A and 4B generally comprises a filter device 210 and a valve entrapment mechanism 215 delivered by a cannula 220 to the interior of the vascular structure 222; a deployable valve/filter frame 225; a filter bag 230 attached to the perimeter of deployable valve/filter frame 225; a compliant, soft outer cuff 235 (preferably formed out of a biologically inert material such as Teflon, Dacron, Silastic, etc.) for sealing the filter device 210 against the inner wall of vascular structure 222 when deployable valve/filter frame 225 is expanded; valve leaflets 240, preferably in the form of a blood-impervious material; a center post 250 (preferably formed out of steel or the equivalent) passing across the interior of deployable valve/filter frame 225; a hinge line 255 on valve leaflets 240, connected to center post 250, for permitting valve leaflets 240 to open and close; co-aptation strands 260 extending across the interior of deployable valve/filter frame 225 and providing a seat against which valve leaflets 240 may close during diastole; and a perimeter seal 265 (preferably formed out of expanded Teflon or the like). Perimeter seal 265 acts like a step to help support valve leaflets 240 during diastole.

In addition, it should also be appreciated that soft outer cuff 235 may comprise a radially expandable mechanism (e.g., a balloon, a decompressed sponge, a spring loaded leaflet, etc.) for sealing deployable valve/filter apparatus 205 against the inner wall of vascular structure 222.

FIGS. 5A-5D illustrate operation of deployable valve/filter apparatus 205 of FIGS. 4A and 4B. More particularly, valve/filter apparatus 205 is first inserted through a small incision 270 in the wall of the vascular structure 222 (see FIG. 5A). Then deployable valve/filter frame 225 is deployed (see FIG. 5B). Thereafter, during systole (see FIG. 5C), blood flows through deployable valve/filter frame 225, forcing valve leaflets 240 open, and proceeds through filter bag 230. Any debris contained in the blood is captured by filter bag 230 and thereby prevented from moving downstream past valve/filter apparatus 205. During diastole (see FIG. 5D), when the blood flow momentarily reverses direction, valve leaflets 240 (shown in FIGS. 4A and 4B) close, seating against co-aptation strands 260 (shown in FIGS. 4A and 4B) across the interior of deployable valve/filter frame 225 (shown in FIGS. 4A and 4B). The closed leaflets 240 (shown in FIGS. 4A and 4B) prevent blood from passing back through the valve/filter frame 225 (shown in FIGS. 4A and 4B).

It should also be appreciated that with valve/filter apparatus 205 shown in FIGS. 4A, 4B and 5A-5D, valve leaflets 240 may be attached to structures other than center post 250, e.g., they may be attached to co-aptation strands 260, or to deployable valve filter frame 225, etc. Furthermore, if desired, valve leaflets 240 may be biased closed, or biased open. In addition, valve entrapment mechanism 215 may consist of one or more flaps (not shown), and have a configuration including, but not limited to, a single disk diaphragm (not shown), a semi-lunar configuration (not shown), a gill slit configuration (not shown), a multi-leaflet flap configuration (not shown), etc.

Figure 6A:
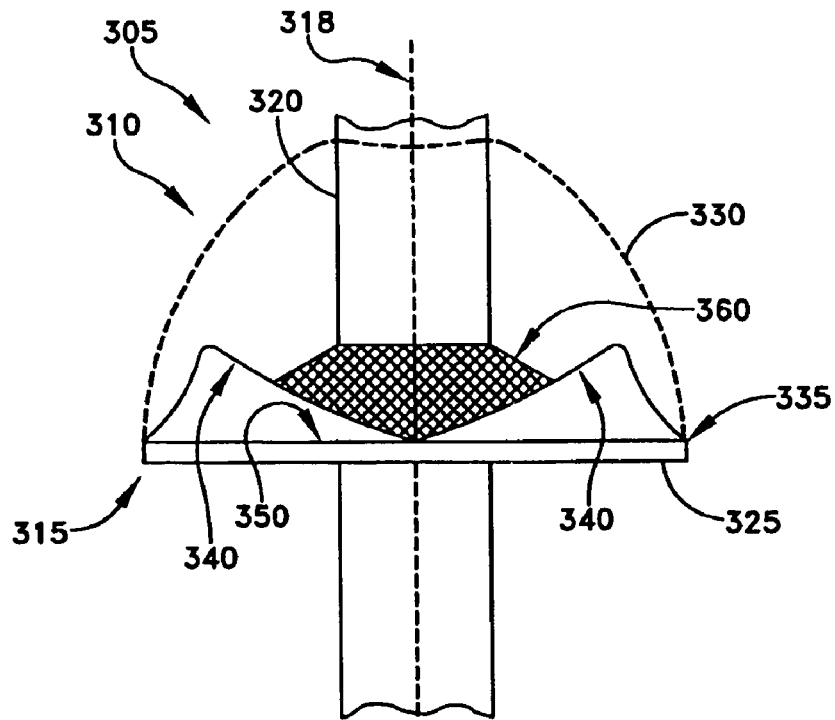
FIGS. 6A-6D are schematic illustrations depicting an orthogonally deployable valve/filter apparatus.
Figure 6B:
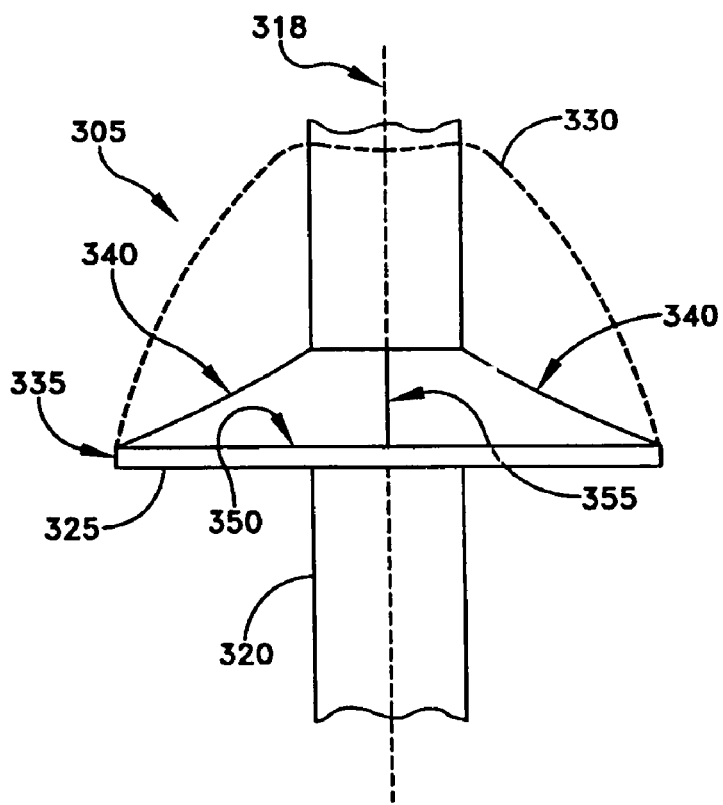
Figure 6D:
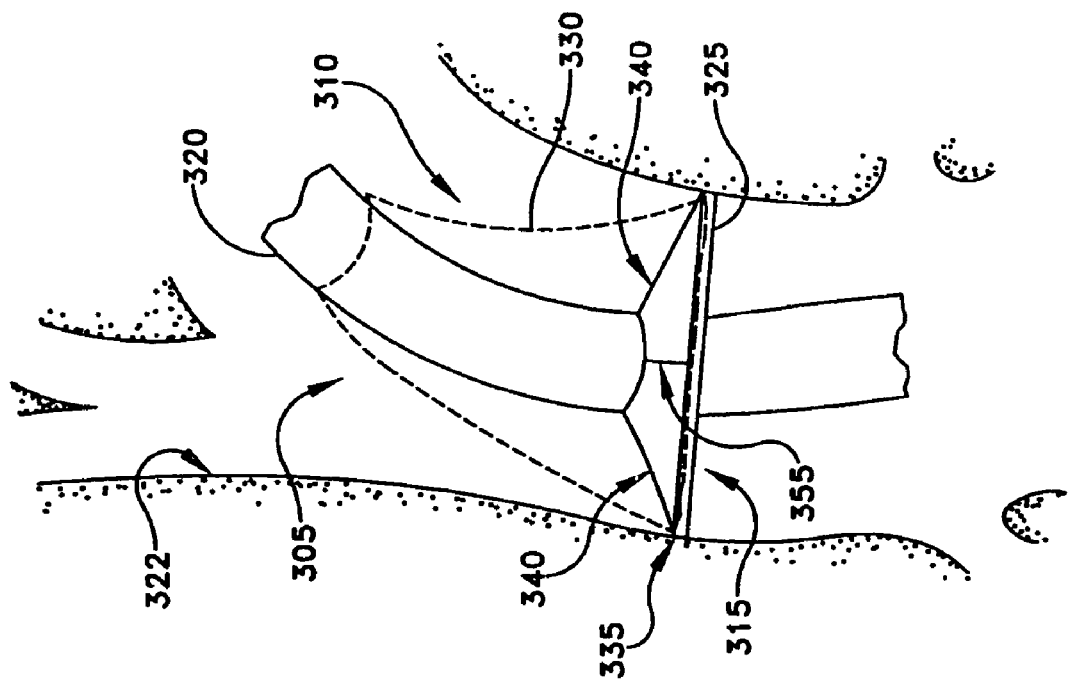
Figure 6C:
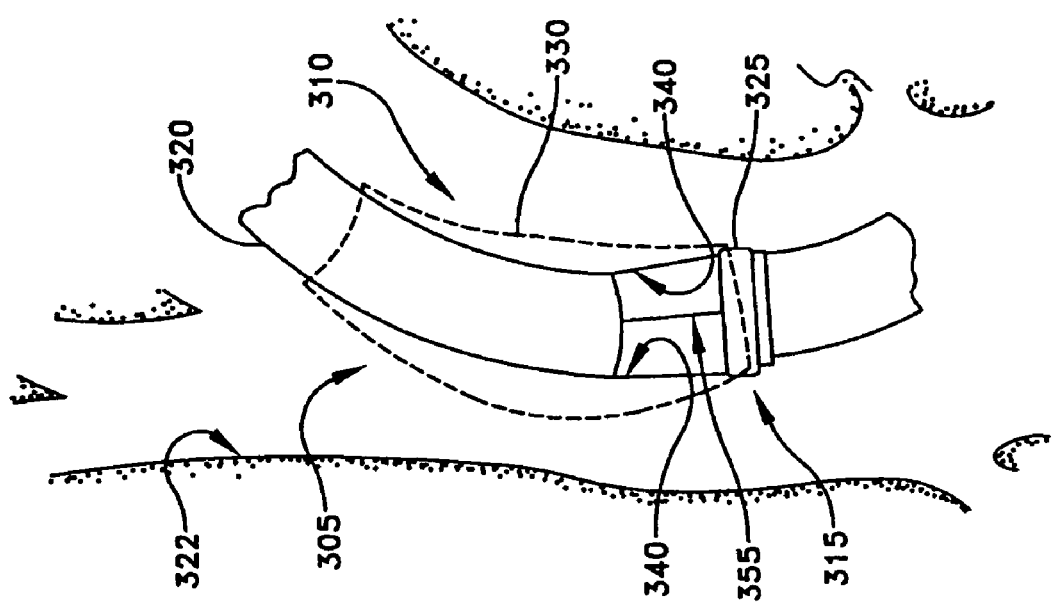

Looking next at FIGS. 6A-6B, there is shown an orthogonally deployable valve/filter apparatus 305. Orthogonally deployable valve/filter apparatus 305 of FIGS. 6A-6D generally comprises a filter device 310 and a valve entrapment mechanism 315 deployed at an angle substantially orthogonal to an axis 318 of a cannula 320, such as a catheter introduced to the vascular system at a location which may be remote from the point of operation, in the interior of a vascular structure 322; a deployable valve/filter frame 325; a filter bag 330 attached to the perimeter of deployable valve/filter frame 325;

a compliant, soft outer cuff 335 (preferably formed out of a biologically inert material such as Teflon, Dacron, Silastic, etc.) for sealing the filter device 310 against the inner wall of vascular structure 322 when deployable valve/filter frame 325 is expanded; valve leaflets 340, preferably in the form of a blood-impervious material, having a first portion 350 in attachment to deployable valve/filter frame 325, and a second portion 355 separable from deployable valve/filter frame 325, so as to allow valve leaflets 340 to open and close; and a mesh material 360 extending across the interior of deployable valve/filter frame 325 and providing a seat against which valve leaflets 340 may close during diastole. In addition, it should be appreciated that mesh material 360 may comprise coaptation strands such as coaptation strands 160 as first shown in FIG. 2A.

In addition, it should also be appreciated that soft outer cuff 335 may comprise a radially expandable mechanism (e.g., a balloon, a decompressed sponge, a spring loaded leaflet, etc.) for sealing orthogonally deployable valve/filter apparatus 305 against the inner wall of vascular structure 322.

In addition, it should also be appreciated that valve entrapment mechanism 315 may be mounted for blood flow in either direction within vascular structure 322.

FIGS. 6A-6D illustrate operation of deployable valve/filter apparatus 305. More particularly, deployable valve/filter apparatus 305 is first inserted through the interior of vascular structure 322 to a desired location (see FIG. 6C). Then deployable valve/filter frame 325 is deployed (see FIG. 6D). Thereafter, during systole (see FIG. 6A), blood flows through deployable valve/filter frame 325, forcing valve leaflets 340 open, and proceeds through filter bag 330. Any debris contained in the blood is captured by filter bag 330 and thereby prevented from moving downstream past deployable valve/filter apparatus 305. During diastole (see FIG. 6B), when the blood flow momentarily reverses direction, valve leaflets 340 close, seating against mesh material 360 across the interior of deployable filter frame 340. The closed leaflets 340 prevent blood from passing back through the valve/filter frame 325.

It should also be appreciated that with valve/filter apparatus 305 shown in FIGS. 6A-6D, valve leaflets 340 may be attached to structures other than deployable valve/filter frame 325, e.g., they may be attached to mesh material 260, or to cannula 320, etc. Furthermore, if desired, valve leaflets 340 may be biased closed, or biased open. In addition, valve entrapment mechanism 315 may consist of one or more flaps (not shown), and have a configuration including, but not limited to, a single disk diaphragm (not shown), a semi-lunar configuration (not shown), a gill slit configuration (not shown), a multi-leaflet flap configuration (not shown), etc.

The filter design as described herein to prevent the escape of captured debris during diastole or filter removal may also be applied to all intravascular filters. Such a filter design may comprise a one-way valve and a filtering mesh in series. Liberated debris may pass through the one-way valve and come to rest in the filtering mesh. The one-way valve ensures permanent entrapment of debris. Potential applications of such an apparatus extend to all percutaneous and surgical procedures on the heart and vascular system, including open heart surgery, balloon dilatation of cardiac valves and arteries, deployment of stents in arteries, diagnostic catheterizations, and other cardiac and vascular procedures. Advantages of such a system include more complete collection of liberated debris, with a resulting decrease in the complications attributable to such debris.

What is claimed is:

1. Apparatus for filtering and entrapping debris from a vascular system of a patient, said apparatus comprising:

a filter device being sized to allow blood flow therethrough and to restrict passage of debris therethrough, and said filter device having a first given perimeter, a proximal side and a distal side; and wherein said filtering device captures debris carried in a first direction of blood flow from said proximal side to said distal side thereof on said proximal side of said filter device;

an entrapment device having a proximal side and a distal side and that is sized to be deployable along with said filter device within the vascular system so as to form a chamber between said distal side of said entrapment device and said proximal side of said filtering device with respect to blood flow through both of said entrapment device and said filtering device, said entrapment device including at least one selective opening of a size to allow passage of debris and blood therethrough, said selective opening allowing passage of blood and debris carried therein therethrough in said first direction of blood flow from said proximal side to said distal side of said entrapment device and from said entrapment device to said filtering device, said selective opening having a restriction element that is operatively provided to change a size of the selective opening without changing the size of the entrapment device as deployed so as to prevent debris passage back through said selective opening from said distal side to said proximal side of said entrapment device in a second direction opposite to said first direction, said selective opening forming a second given perimeter;

wherein said entrapment mechanism allows blood and debris carried therein therethrough in said first direction of blood flow, said filtering device allows blood therethrough in said first direction of blood flow, and said restriction element prevents debris back through said selective opening in said second direction of blood flow opposite to said first direction of blood flow such that said chamber entraps the filtered debris received therein for debris removal from the vascular system of the patient.

2. Apparatus according to claim 1 further comprising an introduction mechanism including a cannula to insert said filter device and said entrapment mechanism into the vascular system of the patient.

3. Apparatus according to claim 1 further comprising a deployable frame being selectively configurable to adjustably size said filter device and entrapment device between a first position and a second position.

4. Apparatus according to claim 3 further comprising a compliant outer cuff being configured to surround said deployable frame, and to make contact with an inner wall of the vascular system of the patient.

5. Apparatus according to claim 4 wherein said compliant outer cuff passively surrounds said deployable frame.

6. Apparatus according to claim 4 wherein said compliant outer cuff is radially expandable.

7. Apparatus according to claim 1 wherein said filter device comprises a filter bag.

8. Apparatus according to claim 1 wherein said entrapment device comprises at least one entrapment leaflet attached on said distal side of said entrapment device and contacting a distal surface on said distal side of said entrapment device such that said at least one entrapment leaflet can be positioned away from said distal surface of said entrapment device to allow blood and debris in said first direction of blood flow therethrough and said at least one entrapment leaflet can be positioned toward said distal surface of said entrapment device to prevent debris in said second direction of blood flow therethrough.

9. Apparatus according to claim 8 wherein said at least one entrapment leaflet comprises a filter material so as to allow blood, and to prevent debris, in said second direction of blood flow back through said entrapment device.

10. Apparatus according to claim 8 wherein said at least one entrapment leaflet comprises a non-porous material so as to prevent blood and debris in said second direction of blood flow back through said entrapment device.

11. Apparatus according to claim 8 further comprising a perimeter seal extending about the interior of said entrapment device so as to provide selectable engagement with said at least one entrapment leaflet in said second direction of blood flow.

12. Apparatus according to claim 8 wherein said distal surface of said entrapment device is provided by a piece of coarse mesh extending across the interior of said entrapment device so as to provide selectable engagement with said at least one entrapment leaflet in said second direction of blood flow.

13. Apparatus according to claim 8 wherein said distal surface of said entrapment device is provided by at least one co-aptation strand extending across the interior of said entrapment device so as to provide selectable engagement with said at least one entrapment leaflet in said second direction of blood flow.

14. Apparatus according to claim 1 wherein said first direction of blood flow is the direction of systolic blood flow and said second direction of blood flow is the direction of diastolic blood flow.

15. Apparatus according to claim 1 wherein said first direction of blood flow is the direction of diastolic blood flow and said second direction of blood flow is the direction of systolic blood flow.

* * * * *